United States Patent

Gordon

[11] Patent Number: 6,022,563
[45] Date of Patent: Feb. 8, 2000

[54] PHENYLBUTAZONE CARRIER FORMULATION

[75] Inventor: Douglas J. Gordon, Pleasant Grove, Utah

[73] Assignee: Superior Equine Pharmaceuticals, Inc., Pleasant Grove, Utah

[21] Appl. No.: 09/240,809

[22] Filed: Feb. 1, 1999

Related U.S. Application Data

[60] Provisional application No. 60/073,707, Feb. 4, 1998.

[51] Int. Cl.⁷ .................................................... A61K 9/16
[52] U.S. Cl. ..................... 424/489; 424/442; 424/484; 424/488; 424/500; 424/502; 514/404
[58] Field of Search ............... 424/442, 484–489, 424/500, 502; 514/404

[56] References Cited

U.S. PATENT DOCUMENTS

| | | | |
|---|---|---|---|
| 3,927,213 | 12/1975 | Lippmann | 424/234 |
| 3,957,803 | 5/1976 | Bodor et al. | 260/295 L |
| 4,455,298 | 6/1984 | McFarlane et al. | 424/95 |
| 5,240,922 | 8/1993 | O'Neill | 574/211 |

OTHER PUBLICATIONS

USPDI—phenylbutazone (veterinary) pp. 2546–2547, 1989.

Merck Veterinary Manual p. 532–535, 1973.

Leer et al :Research in Vet. Scin. vol. 99 #1, pp. 50–56, 1988 (abstract).

Ammal–Pharm #242 p. 18, 1991, Acme capuler.

*Primary Examiner*—Neil S. Levy
*Attorney, Agent, or Firm*—Duft, Graziano & Forest, PC

[57] ABSTRACT

A powdered carrier formulation for delivery of phenylbutazone to animals contains phenylbutazone in combination with a flavoring agent and an anticaking agent.

11 Claims, 2 Drawing Sheets

| | SUCRALOSE | SACCHARINE | ASPARTAME | SUCROSE | GLUCOSE | FRUCTOSE | LACTOSE | ACESULFAME-K |
|---|---|---|---|---|---|---|---|---|
| SOLO FORMULATION | | | 10% | | | | | |
| 2 SWEETENER COMBINATION | | 6% | 4% | | | | | |
| 3 SWEETENER COMBINATION | | | 6% | | 2% | | 2% | |
| 4 SWEETENER COMBINATION | 1% | 5% | | 2% | | 2% | | |
| 5 SWEETENER COMBINATION | 1% | | 3% | | 2% | | 2% | 2% |
| 6 SWEETENER COMBINATION | 1% | 3% | 3% | | | 1% | 1% | 1% |
| 7 SWEETENER COMBINATION | 1% | 1% | 3% | 1% | 1% | | 1% | 1% |
| 8 SWEETENER COMBINATION | 1% | 2% | 2% | 1% | 1% | 1% | 1% | 1% |

FIG. 2

PHENYLBUTAZONE CARRIER FORMULATION

RELATED APPLICATIONS

This application is a continuation in part of provisional application No. 60/073,707 filed on Feb. 4, 1998.

FIELD OF THE INVENTION

The invention relates to anti-inflammatory drugs and in particular, to a new and improved carrier formulation for delivery of phenylbutazone and functional homologues thereof. More specifically the carrier is palatable to horses, provides improved absorption into the horse's blood stream, and facilities new methods of preparing and administering phenylbutazone to horses.

PROBLEM

Phenylbutazone, is one of the most popular and useful nonsteroidal anti-inflammatory veterinary pharmaceuticals. It is typically the drug of choice for equine treatment modalities when an illness or injury necessitates the use of a painkiller or anti-inflammatory medication. Phenylbutazone treats joint deterioration, swelling and inflammation from injuries, founder, fevers, and various other pains experienced by horses.

While phenylbutazone has been used to treat horses for more than thirty years, the administration of phenylbutazone persists in being the source of many problems. Despite its bitter taste, phenylbutazone is most often administered orally. The horses often reject the bitter drug, which leads to inconsistent dosages and extreme inconvenience suffered by those administering the drug.

Phenylbutazone is typically available to horse owners and veterinarians in one-gram tablets for oral administration. Horses do not willingly eat phenylbutazone tablets. Absent physical force, most horses will not swallow phenylbutazone tablets due to their bitterness. Thus, administration involves first catching the horse and, depending on the individual personality and training of the horse, applying various degrees of restraints. Restraints range from a halter to prevent bobbing and weaving of the head, to more extreme measures that prevent rearing and kicking.

Horse owners and veterinarians have developed several means for the actual delivery of phenylbutazone to horses. In simple cases the tablets are crushed and mixed with the horse's food. This method is problematic because the crushed tablets do not adhere to the horse's food. Powder or granules sift to the bottom of the feeder as the horse eats. The amount of sifting varies with each administration and results in inconsistent dosages or diet problems due to the addition of feed to administer the remaining medication.

Some horses reject the grain and drug mixture altogether, requiring the additional step of mixing the crushed tablet with syrup or molasses before adding the bitter drug to the horse's feed. This method is problematic for several reasons. Syrup and molasses are very sticky, and the mixing process leaves a mess in the surrounding area as well as in the mixing container and feed trough or dish. In addition, the phenylbutazone is insoluble in syrup and molasses making it impossible to obtain a homogeneous mixture. If the mixture is not immediately administered to the horse, the phenylbutazone settles resulting in an inconsistent dosage or additional mixing requirements. Encapsulation of the crushed tablet matter by the syrup or molasses also hinders the speed at which digestive fluids can interact with the phenylbutazone and, consequently, blood absorption of phenylbutazone is delayed through the digestive process.

In other cases the delivery means includes mixing the crushed tablets with water in a slurried form for oral administration with a syringe. This method of delivery often requires the person administering the dosage to reach into the horse's mouth and exert pressure at certain points as inducement for the horse to open its mouth for direct delivery of the drug to the horse's throat by syringe. This activity is unpleasant for the horse and the person, and can result in injury as the person administering the drug is bitten, pawed or stepped on by a stubborn horse. Because the slurry is still bitter, a horse will continue to reject the slurry with efforts that increase in intensity over time. Ultimately, it becomes difficult or impossible to catch the horse three times a day for delivery of the drug and, if caught, the horse attempts to spit out the slurry after it is delivered.

Paste and granulized formulations of phenylbutazone are available to prevent those administering the drug from having to crush tablets, but the granulized and past formulations still sustain the same problems associated with tablets, namely, rejection, inconvenience, and inconsistent dosages. For example, The paste is squeezed from a tube into the rear of the oral cavity under the horse's tongue. Most horses make a valiant effort to spit the paste out. Thus, the horse's mouth must be empty during delivery so the paste adheres to the oral cavity to prevent it from being spit out. If, as often is the case, the horse has hay or grain residue in its mouth at the time of delivery, the paste will adhere to it and is easily spit out along with the hay or grain. Some horses even learn to rinse their mouth out after delivery causing owners to limit access to water for approximately 15 minutes.

The described administration problems with phenylbutazone would be merely inconvenient, except that they, in turn, cause serious problems, which are related to effective dosages. The drug is intended to control potentially chronic inflammation and pain, which can result in permanent soft tissue lesions, such as scarring of other fibroid tissue growth, as a consequence of long term chronic inflammation cycles. The drug provides relief from chronic cycles of inflammation and pain, and eventually facilitates increased range of motion without permanent loss of function. Thus, it is important to provide a method of administration that avoids peaks and valleys in the blood concentration levels of phenylbutazone arising from inconsistent dosage due to rejection or an inability to catch the horse for administration of the drug.

An important factor to consider in the delivery of phenylbutazone, in addition to methods for oral administration of the drug, is the speed at which the drug is absorbed into the horse's blood. Inflammation and pain are more easily relieved when effective treatment concentrations are attained more quickly. This is especially true when the inflammation is potentially associated with hemorrhaging due to soft tissue injury. Maintaining the proper blood concentration level, timing, and diet are critical to the effectiveness of the drug. Even so, it is commonly understood that mixing a drug with a carrier, such as a nutritional base for delivery of the drug, has the disadvantage of slowing down the blood absorption rate.

While a veterinarian should make the determination on an individual basis, a moderate dose for a 1000 pound horse is 1–2 grams or 5–10 cc per administration. Oral administration of phenylbutazone is slow to take effect, requiring 3–5 hours to achieve an effective concentration level. Three dosages per day should be administered to maintain the proper blood concentration level. However, due to the problems with oral administration, most horse owners and veterinarians settle for a double or sometimes only a single dosage per day, as opposed to the ideal triple dosage.

Another problem related to dosage is measuring the proper amount of medication for the horse. Where the paste formulation is used, the person administering it must premeasure the paste or guess at the appropriate amount as it is squeezed into the horse's mouth. Both techniques result in an inconsistent dosage either from guesswork or due to loss of medication from residue left behind as the paste is transferred from the measuring device to administering device. In the tablet form, an odd dosage requires splitting the tablet, which results in inconsistent dosages due to crumbling of the tablets.

Administration and dosage problems are compounded where prolonged treatments are required for treatment of chronic soft tissue injuries, and these problems can result in significant health effects to the horse and cost burden on the owner. Therefore, there is a need for an improved carrier formulation of phenylbutazone that is palatable to horses, easily administered in a proper dosages without special skills or alteration from its manufactured state, and provides quicker absorption into the bloodstream.

SOLUTION

The present invention overcomes the problems that are outlined above and advances the art by providing an improved carrier formulation for administering phenylbutazone in a palatable medium to horses. The carrier formulation comprises a powdered carrier base including at least one flavoring agent and at least one anti-caking agent mixed to substantial homogeneity with a therapeutically effective amount of phenylbutazone. The powder carrier base and phenylbutazone mixture is palatable to horses providing owners and veterinarians with confidence that their horse will consume the full dosage of medication.

Phenylbutazone is commonly known in the art and is described in U.S. Pat. No. 2,562,830. Phenylbutazone is also known as 4-butyl-diphenyl-3,5-pyrazoidinedione, benzone, butadione, intrabutazone, and numerous other common names. Phenylbutazone is widely understood to be an effective veterinary anti-inflammatory and analgesic agent in treating inflammation in horses and other animals. A review of the hematological effects of phenylbutazone has been published by G. A. Faich in 7 Pharmacotherapy 25 (1987). There are numerous commercial suppliers of phenylbutazone including, by way of example, Sigma Corporation located in St. Louis, Mo.

The flavoring agent is an inactive ingredient comprising a flavoring agent and an anticaking agent. The flavoring agent is a plurality of sweeteners and flavor additives that make the powdered carrier formulation palatable to horses as a food supplement and in its raw form. Horses consider that phenylbutazone delivered with the carrier formulation as a treat, and they aggressively ingest it Sweeteners used in the flavoring agent may be any type of compatible sweetener, either from a natural material or an artificially produced sweetener. Artificial sweeteners such as saccharine and aspartame are preferred for cost reasons, and because unlike natural sugars, they do not promote significant tooth decay and contribute few if any calories to the foods they sweeten. Commercial suppliers of Saccharine and aspartame include Monsanto Corporation and its subsidiaries, such as Kelco Corporation. In addition, because horses have preferred tastes, combinations of sweeteners may be employed to ensure palatability in a broader range of horses. Examples of sweeteners include but are not limited to, sucrose, glucose, fructose, lactose, acesulfame-K, dextrose, sucralose, saccharin, and aspartame.

Flavor additives used in the flavoring agent may also be products from a natural material or synthetically produced products. Any flavor additive palatable to horses including but not limited to, cinnamon, orange, or apple, may be employed. Preferably, however, inventors have found artificial green apple flavoring, such as that which is commercially available from Professional Compounders Center of America, to be the most palatable to the broadest range of horses. Additional examples of flavor additives include but are not limited to cinnamon, cherry, strawberry, and carrot.

The anti-caking agent is not a necessary ingredient to the carrier formulation of the present invention, and is utilized for the practical requirement of improving the manufacturing process. The preferred anti-caking agent is silica dioxide sold under the trade name Flogard, an example of which can be purchased from Pharmatech Inc. The anti-caking agent improves the manufacturing process by preventing clotting and balling of the product caused by the inherently tacky nature of the flavoring ingredients. It should also be noted that, while the anti-caking agent silica dioxide is added to the carrier formulation to improve manufacturing, additional anti-caking agents are present as sub-ingredients in some of the flavoring ingredients. For example, calcium silicate is a sub-ingredient of the Fresh Green Apple flavoring ingredient.

Despite common knowledge that dilution of a drug with a carrier for delivery has the disadvantage of slowing down the blood absorption rate, the dilution of the phenylbutazone active agent with the carrier formulation of the present invention substantially improves blood absorption during the initial hours after administration. Not only is the initial delivery speed faster with the carrier formulation, but absorption and metabolization of the phenylbutazone over subsequent intervals is approximately equivalent to that of delivery of pure phenylbutazone.

The respective ingredients of the carrier formulation are provided as a solid, powder, or particulate at room temperature, so that mixing of the materials results in a finely divided powder. The powder has an electrostatic affinity for the cellulosic substances that horses eat.

The carrier formulation is produced by causing particles of the at least one flavoring agent and the at least one anti-caking agent to come into high speed contact with particles of the therapeutically effective amount of phenylbutazone by collision. During collision of the particles there is a partial melting and fusion with each other to form an agglomerate of all the particles in a substantial homogenous mixture of fine powder at room temperature. Various apparatuses can be utilized to realize contact of the ingredients, including but not limited to V shaped blenders, slant load blenders, high efficiency powder mixers, and pneumatic high vortex apparatuses and so on. It is possible to effect the colliding contact of the ingredients by subjecting them to a single blending process. Nevertheless, multiple blending obtains an increase in the melting, fusion, and homogeneity performance yielding an overall better mixture.

Care must be paid here to determine the proper blending time, as the blending times will vary depending on the device and its efficiency. Blending is performed until the phenylbutazone is distributed to substantial homogeneity in the carrier base. A suitable weight proportion of phenylbutazone to achieve the advantages of the invention may be in the range of 50% to 90% and preferably in the range of 70% to 90% of the total formulation weight. An even more preferable weight is in the range of 75% and 90% with an even more preferable range being 85% to 90%. A suitable weight proportion of anti-caking agent is in the range of 0% to 10% but preferably 4%, depending upon the type of anticaking agent that is used. A suitable weight proportion of the flavoring ingredient may be in the range of 10% to 50% but preferably ranges from 10% to 20%.

The carrier formulation of the present invention is administered to horse orally in its raw form or as a feed supplement by spreading it over conventional feed components, including but not limited to, grain, hay, oats, barley, corn and so on. Advantageously, the sweetener ingredients provide the carrier formulation with an inherently tacky property, such that the carrier formulation adheres to feed when the it is administered as a feed supplement. Thus, product is not lost due to sifting as the horse eats.

BRIEF DESCRIPTION OF THE DRAWING

FIG. 2 illustrates examples of sweetener combinations by percentage of total weight of the carrier formulation of the present invention.

DETAILED DESCRIPTION

Figure 1:
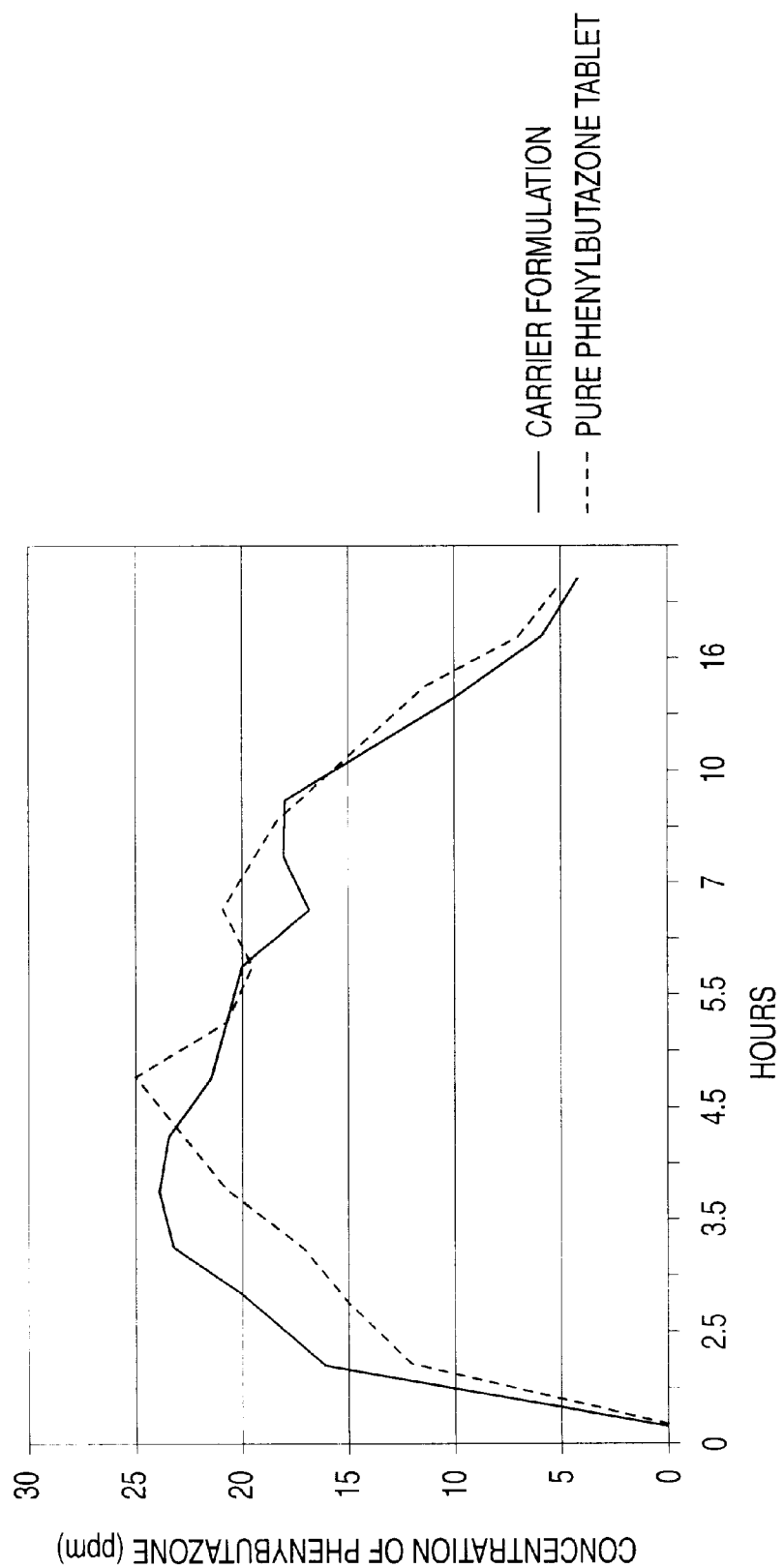
FIG. 1 presents data from a comparative test study showing phenylbutazone blood concentrations over time between a group of horses that were fed phenylbutazone with the carrier formulation according to the present invention versus a group of horses that were fed phenylbutazone from a prior art formulation.

The following non-limiting examples set forth preferred methods and materials for making the phenylbutazone carrier formulation according to the present invention. In addition, the phraseology and terminology employed herein is for the purpose of description, and not of limitation.

EXAMPLE 1

A PREFERRED PRODUCT FORMULATION

During the first stage of preparation, seven individual batches of product were mixed, each having a total weight of 124 kilograms. A 200 kilogram stainless steel blending mixer, commonly known in the art as a V-shaped blender, was used to mix each batch. Before each batch was mixed the blending mixer was sterilized by thoroughly wiping with a sterile cloth soaked in rubbing alcohol. During the second stage of preparation, the seven individual batches were combined and mixed in a 1000 kilogram stainless steel V-shaped blending mixer to produce the finished product.

Each of the seven batches produced during the first stage of preparation consisted of: 100 kilograms of phenylbutazone, 10 kilograms of saccharine, 6 kilograms of Fresh Green Apple Flavor, 4 kilograms of Aspartame, and 4 kilograms of Flogard. The ingredients for a single batch were weighed and placed in the 200 kilogram blending mixer and blended for a period of 40 minutes. After 40 minutes of blending, the batch was removed from the 200 kilogram blending mixer and weighed to confirm that no product was lost. After weighing the batch was placed into a 1000 kilogram blending mixer, but was not mixed until all seven batches from the first stage of preparation were added to the 1000 kilogram mixer.

During the second stage of production the seven batches were blended in the 1000 kilogram blender for a period of 20 minutes to produce 868 kilograms of finished product. After blending, the finished product was removed and weighed to confirm that substantially no product was lost. After weighing, the product was tested for bacteria and potency before packaging in individual doses. The packaged product contained 1 gram of phenylbutazone, 0.1 gram of Saccharine, 0.06 gram of Fresh Green Apple Flavor, 0.04 gram of Aspartame, and 0.04 gram of Flogard, per 3.5 cc spoonful of packed powder.

EXAMPLE 2

BIOEQUIVALENCE TEST

In example two, three healthy mature geldings and a non-pregnant mare aged 3–10 years with similar weights were chosen for a bioequivalence test. The bioequivalence test was designed to determine the difference in blood plasma absorption between commercially available phenylbutazone tablets and the product of example one.

Two weeks prior to the test, the horses did not receive any form of medication. At five o'clock p.m. the evening before the test, each horse was fed a normal meal consisting of 1 gallon of grain with twelve percent protein, and ten pounds of alfalfa hay. During the test each horse was stabled separately and had access to drinking water at all times. On test day, each horse was fasted until five hours after administration of the test product, and then given a normal meal consisting of one gallon of grain with twelve percent protein and ten pounds of alfalfa hay. Each horse was again given a normal meal consisting of one gallon of grain with twelve percent protein and ten pounds of alfalfa hay at five hours and at twelve and one-half hours after administration.

The morning of the test, 4.96 grams of the product from example one containing a total of four grams of phenylbutazone, was dissolved in one quart of water. The dissolved mixture of product and water was then tubed directly into the horse's stomach. Without removing the tube, a follow up quart of water was also tubed directly into the horse's stomach to flush out the tube and mixing bucket. Each of the three horses followed this procedure.

Two hours following administration a 4.5 cc blood sample was taken from each of the three horses. Thereafter, additional 4.5 cc blood samples were taken at half-hour intervals until the sixth hour. After the sixth hour 4.5 cc blood samples were taken hourly until the eighth hour. After the eighth hour 4.5 cc blood samples were taken at twelve and one-half hours, sixteen hours, and eighteen hours. The blood samples were taken with a 20 gauge needle and promptly put into a green CST Lithium Heparin tube and refrigerated at 40 degrees F. After all of the samples were collected, the blood samples were spun to separate the blood plasma from each sample. The separated blood plasma was placed in a freezer for twenty-four hours.

After twenty-four hours, the blood plasma was thawed to room temperature and phenylbutazone levels were quantified for each sample by a validated HPLC method. The average phenylbutazone level for the three horses at each of the sampling time intervals are given in Table 1.

COMPARISON TO PHENYLBUTAZONE TABLETS

The same test population of horses was used to monitor phenylbutazone blood plasma levels from commercially available phenylbutazone tablets. Subsequent to the first test and before the comparison test using prior art phenylbutazone tablets was performed, approximately fifteen half lives of phenylbutazone, or seventy five hours, passed. The half-life of phenylbutazone is four to five hours. After seventy five hours the steps of the prior test were repeated exactly, except that four 1 gram tablets of phenylbutazone (4 grams of pure phenylbutazone) were substituted for the 4.96 grams of product from example one. Thus, both tests administered a total of four grams of phenylbutazone per horse. The average phenylbutazone level for the three horses in the second test are also given in table 1.

TABLE 1

BLOOD PLASMA CONCENTRATIONS OF PHENYLBUTAZONE

| Number of Hours after administration | Average phenylbutazone concentration for product of example one (ppm) | Average phenylbutazone concentration for pure phenylbutazone (ppm) | Percent Difference in Intestinal Absorption |
|---|---|---|---|
| 2 | 15.75 | 11.72 | 34% |
| 2.5 | 19.14 | 14.63 | 31% |
| 3 | 23.16 | 16.90 | 37% |
| 3.5 | 23.81 | 20.59 | 16% |
| 4 | 23.37 | 22.59 | 3% |
| 4.5 | 21.46 | 24.91 | −14% |
| 5 | 20.66 | 20.59 | 0% |
| 5.5 | 20.02 | 19.57 | 2% |
| 6 | 16.69 | 20.98 | −20% |
| 7 | 17.94 | 19.30 | −7% |
| 8 | 17.92 | 17.39 | 3% |
| 10 | 13.80 | 14.25 | −3% |
| 12.5 | 9.24 | 11.26 | −18% |
| 16 | 5.73 | 6.84 | −16% |
| 18 | 4.23 | 4.79 | −12% |

FIG. 1 illustrates a graphical representation of the data contained in Table 1. From FIG. 1 and Table 1, it follows that phenylbutazone administered with the carrier formulation exhibited superior bloodstream absorption during the initial hours following administration. Specifically, the phenylbutazone delivered with the carrier formulation was absorbed on average 34% faster during the first three hours and 24.2% faster during the first four hours. During subsequent intervals, the phenylbutazone levels remained approximately equivalent to those of the pure phenylbutazone delivery.

The time that is required for a drug to enter the bloodstream corresponds to the time required for pharmacological efficacy. Presently, oral doses of pure phenylbutazone require approximately three to five hours to take effect. This is verified by Example 2 showing the average peak concentration of 24.91 ppm occurring at four and a half hours for the phenylbutazone tablets.

This example shows that the initial time for phenylbutazone to take effect is shortened when the phenylbutazone is delivered by the carrier formulation, yet metabolization over extended periods remains substantially the same. In addition, the average peak concentration of 23.81 ppm for phenylbutazone delivered by the carrier formulation occurs at three and a half hours, which closely corresponds to the recognized therapeutic dosage interval of four hours. Thus, consistent blood concentration levels are maintained throughout a treatment period because subsequent dosages are administered as the metabolization of absorbed phenylbutazone begins.

Inventors also believe that additional advantages will be realized by quicker absorption of the phenylbutazone. Phenylbutazone is an irritant with known side effects such as stomach and/or intestinal ulceration. Inventors believe that faster absorption of the phenylbutazone across the stomach lining following administration will reduce known side effects by lessening contact with body tissue.

EXAMPLE 3

PALATABILITY TEST

In example 3, two hundred and fifty racehorses were randomly selected for a palatability test of phenylbutazone delivered by the carrier formulation of example one. The test was conducted over three days while the horses were undergoing race training.

During the test, a single dosage of 2.48 grams of the product from example one, containing two grams of phenylbutazone, was mixed with each horse's evening feed. The evening feed consisted of two gallons of grain mixed with one ounce of liquid vitamin.

The result for all two hundred and fifty horses over the course of the three day study was a 0.75% rejection rate. This compares to a 100% rejection rate for pure phenylbutazone. A rejection for purpose of this test was defined as an individual horse's refusal to voluntarily finish eating its entire evening feed.

EXAMPLE 4

Example 4 illustrates a plurality of formulations, for the carrier formulation of the present invention. The formulations were all prepared according to the method of example 1 and comprise 4% silica dioxide anti-caking agent, 6% green apple flavor additive, and a therapeutically effective amount of phenylbutazone. Although various weight percentages will be apparent to one skilled in the art based on the description given herein, the formulations of this example were mixed so that the sweetener ingredient or combination of sweetener ingredients was 10% of the total formulation weight. FIG. 2 illustrates the examples of sweetener combinations for the carrier formulation prepared in example 4.

It is apparent that there has been described, an improved carrier formulation for the delivery of phenylbutazone, that fully satisfies the objects, aims, and advantages set forth above. While the carrier formulation has been described in conjunction with a specific embodiment thereof, it is evident that many alternatives, modifications, and/or variations can be devised by those skilled in the art in light of the foregoing description. Accordingly, this description is intended to embrace all such alternatives, modifications and variations as fall within the spirit and scope of the appended claims.

What is claimed is:

1. A carrier formulation for delivery of phenylbutazone and functional homologues thereof to horses, consisting essentially of:

a powdered carrier selected from the group consisting of sweeteners, flavoring agents, anti-caking agents and combinations thereof; and a therapeutically effective amount of phenylbutazone for the treatment of equine ailments selected from the group consisting of joint deterioration, swelling and inflammation, founder, and fevers, said phenylbutazone being dispersed to homogeneity in said powdered carrier in an amount ranging from 50% to 90% by weight of the formulation.

2. The carrier formulation as set forth in claim 1, wherein said powdered carrier includes a plurality of non-sugar sweeteners selected from the group consisting of saccharin, aspartame, and acesulfame potassium.

3. The carrier formulation as set forth in claim 1, wherein said powdered carrier base in combination with said phenylbutazone are present in effective amounts for accelerating blood absorption of phenylbutazone in equine blood subsequent to oral consumption of said carrier formulation, wherein acceleration of blood absorption is determined with respect to phenylbutazone alone.

4. The carrier formulation as set forth in claim 1, wherein said powdered carrier in combination with said phenylbutazone are present in effective amounts so as to be palatable to horses as a feed supplement and without addition of an additive medium.

5. The carrier formulation as set forth in claim 2, wherein said flavoring agent includes a flavor selected from the group consisting of cinnamon, cherry, strawberry, carrot, and orange flavors.

6. The carrier formulation as set forth in claim 2, wherein said flavoring agent includes apple flavor.

7. The carrier formulation as set forth in claim 1, wherein said phenylbutazone is present in an amount ranging from 75% to 90% of a total weight of the carrier formulation.

8. The carrier formulation as set forth in claim 1, wherein said phenylbutazone is present in an amount ranging from 85% to 90% of a total weight of the carrier formulation.

9. A method of administering phenylbutazone to an animal, said method comprising the steps of:

obtaining a carrier formulation consisting essentially of powdered carrier selected from the group consisting of sweeteners, flavoring agents, anti-caking agents and combinations thereof, and a therapeutically effective amount of phenylbutazone for the treatment of equine ailments selected from the group consisting of joint deterioration, swelling and inflammation, founder, and fevers, wherein said phenylbutzone is dispersed to homogeneity in said carrier in an amount ranging from 50% to 90% by weight of the formulation;

feeding the carrier formulation to horses.

10. The method as set forth in claim 9, wherein said animal is a horse.

11. The method as set forth in claim 10, wherein said step of obtaining a carrier formulation includes obtaining a carrier formulation wherein said powdered carrier base in combination with said phenylbutazone are present in effective amounts for accelerating blood absorption of phenylbutazone in equine blood subsequent to oral consumption of said carrier formulation, where acceleration of blood absorption is determined with respect to phenylbutazone alone, and after said step of feeding the carrier formulation there occurs a further step of waiting for accelerated blood absorption of phenylbutazone in said horse.

* * * * *